(12) United States Patent
Lee

(10) Patent No.: US 9,220,801 B2
(45) Date of Patent: Dec. 29, 2015

(54) AIR PURIFYING APPARATUS USING MICROWAVES

(71) Applicants: Yeon Su Lee, Daejeon-si (KR); Dae Gon Han, Daejeon-si (KR)

(72) Inventor: Yeon Su Lee, Daejeon-si (KR)

(73) Assignees: Yeon Su Lee, Daejeon (KR); Dae Gon Han, Daejeon (KR)

( * ) Notice: Subject to any disclaimer, the term of this patent is extended or adjusted under 35 U.S.C. 154(b) by 0 days.

(21) Appl. No.: 14/288,961

(22) Filed: May 28, 2014

(65) Prior Publication Data

US 2015/0004063 A1    Jan. 1, 2015

(30) Foreign Application Priority Data

Jun. 26, 2013  (KR) .......................... 10-2013-0074017

(51) Int. Cl.
*B03C 1/00* (2006.01)
*B01D 24/00* (2006.01)
*A61L 9/16* (2006.01)

(52) U.S. Cl.
CPC ........................................ *A61L 9/16* (2013.01)

(58) Field of Classification Search
CPC ............. A61L 9/00; A61L 9/014; A61L 9/18; A61L 9/205; A61L 9/20
USPC .................... 422/21; 250/492.1; 96/1; 55/523
See application file for complete search history.

(56) References Cited

U.S. PATENT DOCUMENTS

2010/0050619 A1 *  3/2010  Colvin et al. ................... 60/311

FOREIGN PATENT DOCUMENTS

| JP | 05-141220 A | 6/1993 |
| JP | 07-222912 A | 8/1995 |
| JP | 2009-240863 A | 10/2009 |
| KR | 10-2008-0062624 A | 7/2008 |

* cited by examiner

*Primary Examiner* — Monzer R Chorbaji
(74) *Attorney, Agent, or Firm* — Novick, Kim & Lee, PLLC; Jae Youn Kim

(57) ABSTRACT

In an air purifying apparatus for removing contaminants, such as soot and the like, by burning contaminated air while passing the contaminated air through a filter heated by microwaves, the apparatus includes: a housing, which is hollow, and comprises an inlet on one side and an outlet on the other side; a ceramic filter of a longitudinal material, which is arranged in the housing in a longitudinal direction of the housing, and includes a plurality of partition walls formed so that a flow path where contaminated air flows may be divided in plurality; and a microwave generator configured to generate microwaves to be supplied to one end surface of the ceramic filter in a longitudinal direction thereof to heat the one end surface of the ceramic filter in the longitudinal direction.

7 Claims, 4 Drawing Sheets

AIR PURIFYING APPARATUS USING MICROWAVES

CROSS-REFERENCE TO RELATED APPLICATION(S)

This application claims priority from Korean Patent Application No. 10-2013-0074017, filed on Jun. 26, 2013, in the Korean Intellectual Property Office, the entire disclosure of which is incorporated herein by reference for all purposes.

BACKGROUND

1. Field

The following description generally relates to an air purifying apparatus using microwaves, and more particularly to an air purifying apparatus, which is installed in a duct where air flows, and removes contaminants by burning contaminated air while passing the contaminated air through a filter heated by microwaves.

2. Description of the Related Art

Most homes or businesses are provided with basic ventilation systems to forcibly remove indoor contaminated air to the outside. More specifically, a range hood mounted above a cooking counter or a ventilator mounted on a ceiling or a wall draws in contaminated air and releases the air to the outside through a duct where air flows.

In such duct, an air purifying apparatus is installed, in which multiple-plate filters such as a prefilter, a carbon filter, a HEPA filter, or the like are sequentially arranged to remove dust, soot, odor, and the like contained in the indoor air. However, as can be seen from the air purifying apparatus, which includes various filters, such filter-type air purifying apparatus installed in a conventional duct tends to put a bigger emphasis on filtering polluted materials such as dust, and thus, it is not suitable for purifying odor, soot, bacteria, and the like contained in polluted air. Further, the filter-type purifying apparatus increases maintenance costs, as filters are needed to be cleaned and replaced on a regular basis, and if not properly cleaned, the filters may not purify air efficiently.

In order to solve the above problems, utility model patent No. 20-365713 discloses a combustible dust collector, in which a combustion heater for burning dust, odor, and the like, and a water tank for filtering burned ashes are installed.

However, the collector also has problems in that a combustion heater, which is heated by electric heat of heat wires, loses heat to the outside, such that combustion efficiency may be reduced and safety may not be guaranteed. Further, in such collector, the combustion heater is not precisely structured, and due to a short length of stay in the combustion heater, contaminated air does not stay long enough to be burned properly, such that filtering efficiency may be reduced. In addition, a water tank for filtering burned ashes may not be installed in a limited space, leading to an increased cost of initial installation, and it would be cumbersome to regularly maintain the water tank.

SUMMARY

In order to solve the above problems, an air purifying apparatus using microwaves is provided, in which contaminated air is heated at a high temperature to be discharged to the outside, so that contaminants contained in the air, such as soot and the like, may be combusted and removed, thereby enhancing air purifying efficiency.

In addition, in the air purifying apparatus, a ceramic filter is heated by microwaves, such that energy efficiency may be improved, and safety may be guaranteed.

In one general aspect, there is provided an air purifying apparatus for removing contaminants by burning contaminated air while passing the contaminated air, the apparatus including: a housing, which is hollow, and includes an inlet on one side and an outlet on the other side; a ceramic filter of a longitudinal material, which is arranged in the housing, and through which the contaminated air passes; and a microwave generator configured to generate microwaves and to supply the generated microwaves to one end surface of the ceramic filter in a longitudinal direction thereof to heat the one end surface of the ceramic filter in the longitudinal direction.

A shielding member may be mounted between the ceramic filter and the housing to prevent microwave and air leakage.

The housing may include a shielding net at the inlet or the outlet to prevent microwave leakage.

The microwave generator may be arranged outside the housing, in which an inlet pipe is formed to be connected to the inside of the housing so that microwaves generated by the microwave generator flow into the housing.

A diffusion member may be included in the housing to diffuse the microwaves generated by the microwave generator to transfer the microwaves to the one end surface of the ceramic filter.

The microwave generator may supply microwaves to the other end surface of the ceramic filter in a longitudinal direction thereof to heat the other end surface of the ceramic filter in the longitudinal direction.

As described above, in the air purifying apparatus using microwaves, contaminated air is heated at a high temperature while passing through a filter, before being discharged to the outside, so that contaminants contained in the air, such as soot and the like, may be combusted and removed, thereby enhancing air purifying efficiency.

In addition, in the air purifying apparatus, a ceramic filter is heated by microwaves, such that energy efficiency may be improved, and safety may be guaranteed. Further, a heater where air passes to be discharged may be omitted, thereby improving anti-corrosion properties and durability of the apparatus. Moreover, microwaves are supplied to the ceramic filter in a longitudinal direction so that an entire area of the filter, through which contaminated air passes, may be heated, thereby improving filtering efficiency of the contaminated air.

Figure 1:
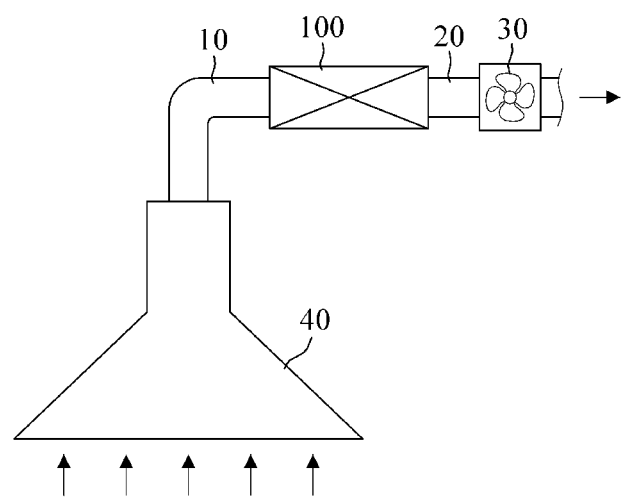
FIG. 1 is a schematic view illustrating an example of a duct in which an air purifying apparatus is installed according to an exemplary embodiment.

Throughout the drawings and the detailed description, unless otherwise described, the same drawing reference numerals will be understood to refer to the same elements, features, and structures. The relative size and depiction of these elements may be exaggerated for clarity, illustration, and convenience.

DETAILED DESCRIPTION

The following description is provided to assist the reader in gaining a comprehensive understanding of the methods, apparatuses, and/or systems described herein. Accordingly, various changes, modifications, and equivalents of the methods, apparatuses, and/or systems described herein will be suggested to those of ordinary skill in the art. Also, descriptions of well-known functions and constructions may be omitted for increased clarity and conciseness.

Figure 2:
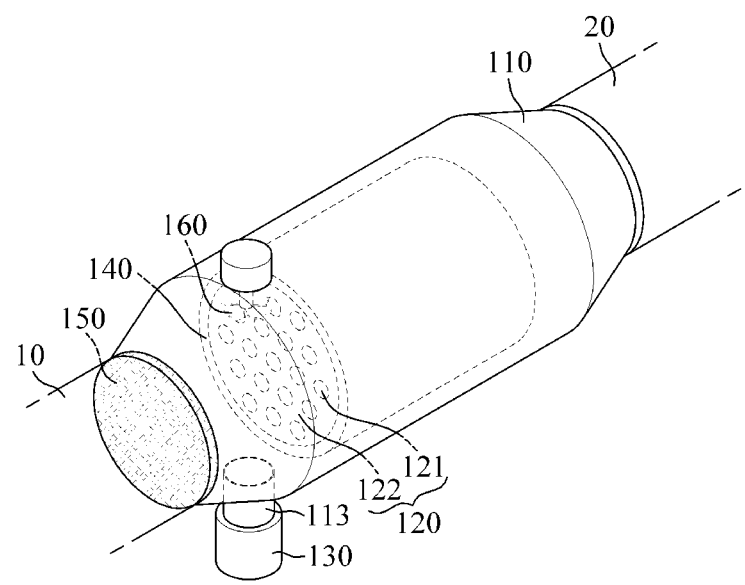
FIG. 2 is a perspective view illustrating an example of an air purifying apparatus according to an exemplary embodiment.
Figure 3:
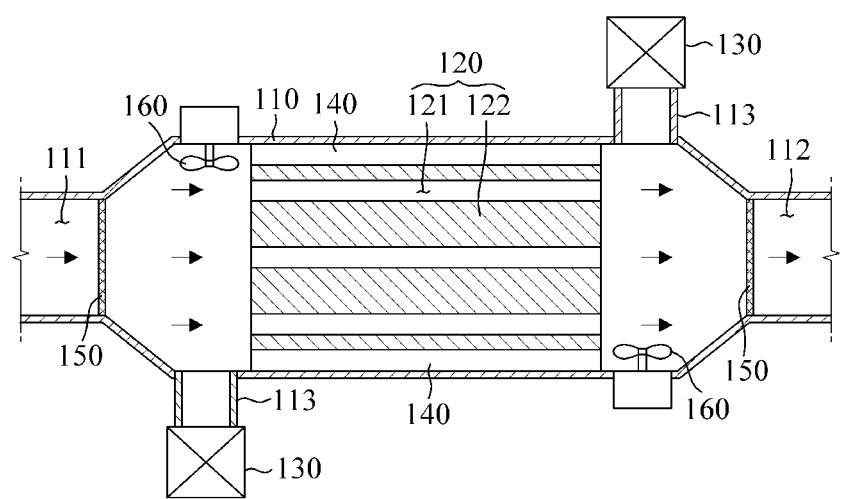
FIG. 3 is a cross-sectional view schematically illustrating an example of an air purifying apparatus according to another exemplary embodiment.
Figure 4:
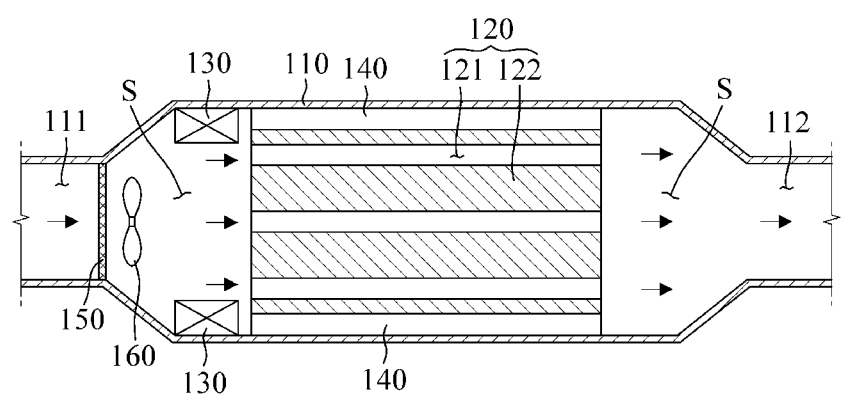
FIG. 4 is a cross-sectional view schematically illustrating an example of an air purifying apparatus according to yet another exemplary embodiment.

According to examples illustrated in FIGS. 1 to 4, an air purifying apparatus is provided to remove contaminants, such as soot and the like, by burning contaminated air while passing the contaminated air through a filter heated by microwaves.

It should be noted that the air purifying apparatus according to an exemplary embodiment may be installed and used alone, or may be used by being installed on a path where air flows such as ducts 10 and 20. Particularly, in ducts 10 and 20, the air purifying apparatus is installed between a first duct 10 and a second duct 20 to release purified air through the second duct 20, or is installed at the end of a duct to release purified air directly to the outside through an outlet of the duct. For convenience, according to an exemplary embodiment, it is assumed that the air purifying apparatus 100 is installed between the first duct 10 and the second duct 20, but the installation thereof is not limited thereto.

Hereinafter, the present disclosure will be described with reference to FIGS. 1 to 4. The air purifying apparatus 100 using microwaves is installed between the first duct 10 and the second duct 20, and removes contaminants by burning contaminated air while passing, through a filter, the contaminated air drawn in by a suction fan 30 or the like. The air purifying apparatus 100 includes: a housing 110, which is hollow, and includes an inlet 111 formed at one side of the housing 10 and connected to the first duct 10, and an outlet 112 formed at the other side of the housing 10 and connected to the second duct 20; a ceramic filter 120 of a longitudinal material, which is arranged in the housing 110 in a longitudinal direction of the housing 110, and includes a plurality of partition walls 122 so that a flow path where contaminated air flows may be divided in plurality; and a microwave generator, which generates microwaves to be supplied to one end surface of the ceramic filter 120 in a longitudinal direction thereof to heat the one end surface of the ceramic filter in the longitudinal direction.

Most homes or businesses generally use a hood 40 mounted above a cooking counter, or a ventilator mounted on a ceiling or a wall, to draw in and discharge contaminated indoor air. In this case, a suction fan 30 mounted on the ducts 10 and 20 provides power to absorb the contaminated air, and the ducts 10 and 20 serve as passages for the absorbed indoor air to be discharged to the outside. According to an exemplary embodiment, the air purifying apparatus 100 is installed in the ducts 10 and 20.

The housing 110 is hollow with a space S formed therein, in which the inlet 111 connected to the first duct 10 is formed on one side to be connected to the space S, and the outlet 112 connected to the second duct 20 is formed on the other side to be connected to the space S. The housing 110 is connected side by side with the first duct 10 and the second duct 20, to supply air flowing in from the inlet 111 through the first duct 10 to the ceramic filter 120 described below, and discharges air filtered by passing through the ceramic filter 120 to the second duct 20 through the outlet 112. The outlet 112 may serve to discharge air, and may be installed on the outside without being connected to the second duct 20. For reference, the inner wall of the housing 110 may be formed of a metal material that reflects microwaves, so that the microwaves supplied by the microwave generator 130 may be reflected on the inner wall of the housing 110, and reacted only on one end surface of the ceramic filter 120.

The ceramic filter 120 may be formed of various porous ceramic materials as long as the materials are reacted with microwaves to be heated at a high temperature. The ceramic filter 120 may be provided as an extruded longitudinal material, and may be arranged in the housing 110 in a longitudinal direction of the housing 110, in which a plurality of partition walls 122 are formed so that the flow path 121 where the contaminated air flows may be divided in plurality. Depending on the shape of the housing 110, the ceramic filter 120 may be formed in a cylindrical shape, or a prism, such as a square prism, or a hexagonal prism.

Since the ceramic filter 120 is made of a porous material, minute particles contained in the air passing through the ceramic filter 20 may be collected, thereby improving air filtering efficiency. Further, as one end surface of the ceramic filter 120 is heated at a high temperature by the microwaves supplied by the microwave generator 130 described below, air that passes through the ceramic filter 120 heated at a high temperature is also heated so that contaminants contained in the air, such as soot and the like, are completely combusted and removed, further improving air purifying efficiency.

The ceramic filter 120 is arranged at the center of the housing 110 in which microwaves are dispersed evenly throughout the front and rear portions of the ceramic filter 120, so that a dispersion space S is formed to supply microwaves on one end surface of the ceramic filter 120.

In order to heat one end surface of the ceramic filter 120, the microwave generator 130 generates microwaves, and supplies the generated microwaves to the one end surface of the ceramic filter 120 in a longitudinal direction. The operation of the microwave generator 130 to heat the ceramic filter 120 may be performed any time a ventilation system, including the suction fan 30, is operated. Further, in some cases, the filtering capability of the ceramic filter 120 may only be used to collect contaminants without operating the microwave generator 130, and the microwave generator 130 may be operated intermittently only if necessary, to heat the ceramic filter 120 to remove contaminants collected in the ceramic filter 120.

For example, the microwave generator 130 may include a magnetron, which is a high-frequency oscillator, and includes a cathode, an anode made of a filament, an antenna, and a magnet. An alternating current voltage of 220V (or 110V), which is generally used, is converted into a high-power voltage of 4000V or above to be supplied to the magnetron, thereby generating microwaves, which oscillate at a high frequency of 2.45 GHz in the magnetron. When these microwaves are radiated along a waveguide into the housing 110, the microwaves are reflected on a metal wall to be absorbed into one end surface of the ceramic filter 120, which is then heated at a high temperature.

According to an exemplary embodiment, the ceramic filter 120 includes a ceramic honeycomb formed of at least one of the following: silicon carbide (SiC), cordierite, or alumina, which are porous ceramic materials.

Among them, a ceramic honeycomb made of SiC in particular has an excellent microwave absorption capability, which may lead to excellent performance in terms of energy efficiency. The ceramic honeycomb using SiC may be manufactured in such a manner that SiC particles are mixed with a solvent or a bonding agent, and the resulting mixture is used for molding, and then, the molded ceramic is calcined. Particularly, the ceramic honeycomb may be manufactured in a manner in which the resulting mixture is extruded to be cut into a specific size, dried, and sintered. In the ceramic honeycomb as prepared in the above manner, a plurality of cells are extended to a specific length to form a minute tunnel, of which an inner wall may have a plurality of holes. In the case of the ceramic filter 120 made of SiC, the microwaves supplied by the microwave generator 130 are not passed but rather absorbed to heat the ceramic filter 120 at a high temperature, thereby enabling an easy molding of a filter.

According to an exemplary embodiment, a shielding member 140 for preventing microwave and air leakage is installed between the ceramic filter 120 and the housing 110. The shielding member 140 shields a space between the ceramic filter 120 and the housing 110 to prevent air that flows into the housing 110 from escaping the housing 110 without passing the ceramic filter 120. Further, the shielding member 140 may have an additional function to prevent the microwaves, which are supplied from the microwave generator 130 to the housing 110, from passing through a space between the ceramic filter 120 and the housing 110. Thus, the shielding member 140 may be made of a metal material to reflect the microwaves.

According to an exemplary embodiment, the housing 110 is provided with a shielding net 150 at the inlet 111 or at the outlet 112 to prevent microwave leakage.

The shielding net 150, which may be made of a metal material, reflects microwaves so as to prevent the microwaves from being leaked into the first duct 10 or the second duct 20. Given that the microwaves have a long wavelength, the shielding net 150 is formed of a metal net, in which each gap of the net is smaller than the wavelength of the microwaves so that the microwaves may not escape. As a result, the air in the first duct 10 flows into the housing 110, while the microwaves in the housing 110 are not leaked into the first duct 10 while being maintained inside the housing 110. Further, the air in the housing 110 is discharged to the second duct 20, while the microwaves in the housing 110 may not be released to the second duct 20 while being maintained inside the housing 100.

According to an exemplary embodiment, the housing 110 is provided with an inlet pipe 113, which is formed to be connected to the inside of the housing 110, and enables the microwaves generated by the microwave generator 130 to flow into the housing 110.

The microwave generator 130 may be mounted in the housing 110, but may also be mounted outside the housing 110 for safety concerns. The inlet pipe 113 connects the housing 110 and the microwave generator 130, enabling the microwaves supplied by the microwave generator 130 to be transferred into the housing 110. For reference, the inner wall of the inlet pipe 113 may be formed of a metal material to reflect microwaves, so that the microwaves supplied by the microwave generator 130 are not absorbed into the inner wall of the inlet pipe 113 but rather reflected to be transferred into the housing 110.

According to an exemplary embodiment, the housing 110 is provided with a diffusion member 160 to transfer the microwaves generated by the microwave generator 130 to one end surface of the ceramic filter 120.

The diffusion member 160 may be manufactured by various known methods, and may include a motor and a fan that rotates while being connected to the motor. The diffusion member 160 diffuses the microwaves generated by the microwave generator 130 so that the microwaves do not converge in a certain area, but rather transferred evenly to one end surface of the ceramic filter 120. Further, the diffusion member 160 may transfer the microwaves to one end surface of the ceramic filter 120 while, at the same time, diffusing the microwaves. Thus, the diffusion member 160 may be mounted on the front side of the ceramic filter 120. For example, the microwave generator 130 may be installed at the lower portion (or upper portion) of the housing 110, and the diffusion member 150 may be installed at the upper portion (or lower portion) of the housing 110.

According to an exemplary embodiment, the microwave generator 130 supplies microwaves to the other end surface of the ceramic filter 120 in a longitudinal direction so as to heat the other end surface of the ceramic filter 120.

As described above, if one end surface and the other end surface of the ceramic filter 120 are heated at the same time, the air flowing through the ceramic filter 120 is heated with certainty, and contaminants, such as soot and the like, are combusted in an effective manner, thereby improving air purifying efficiency. Further, in the above case, only one microwave generator 130 is provided to supply the microwaves to one end surface and the other end surface of the ceramic filter 120, but two or more microwave generators 130 may also be provided, in which case, the microwave generator 130 to supply microwaves to one end surface of the ceramic filter 120 is provided separately from the microwave generator 130 to supply microwaves to the other end surface of the ceramic filter 120. In the case where there are two or more microwave generators 130, the inlet 111 that transfers the microwaves generated by each microwave generator 130 into the housing 110 may be formed separately for the one side and the other side of the housing 110, and the diffusion member 160 that diffuses the microwaves may also be mounted separately for the one side and the other side of the housing 110. In addition, the outlet 112 of the housing 110 may further include the shielding net 150 to prevent the microwaves generated by the microwave generator 130 from being released to the outside through the outlet 112.

Hereinafter, operations performed by the air purifying apparatus using the microwaves described above with reference to FIGS. 1 to 4 will be described below.

Once the suction fan 30 is operated, indoor air is drawn in through the hood 40, and the air is then transferred to the ducts 10 and 20. After passing the first duct 10, the air is supplied through the inlet 111 into the housing 110. At this point, microwaves supplied by the microwave generator 130 are provided to one end surface of the ceramic filter 120, the entire part of which is heated at a high temperature. The air flowing into the housing 110 is filtered while passing the ceramic filter 120 heated at a high temperature, and at the same time, and contaminants contained in the air, such as soot and the like, are simultaneously heated at a high temperature to be combusted and removed. The air purified after passing through the ceramic filter 120 is transferred through the outlet 112 of the housing 110 to the second duct 20 to be discharged to the outside.

As described above, the air purifying apparatus using microwaves, in which contaminated air is heated at a high temperature while passing through a filter, before being discharged to the outside, so that contaminants contained in the air, such as soot and the like, may be combusted and removed, thereby enhancing air purifying efficiency.

In addition, in the air purifying apparatus, a ceramic filter is heated by microwaves, such that energy efficiency may be improved, and safety may be guaranteed. Moreover, microwaves are supplied to the ceramic filter in a longitudinal direction so that an entire area of the filter, through which contaminated air passes, may be heated, thereby improving filtering efficiency of the contaminated air.

A number of examples have been described above. Nevertheless, it should be understood that various modifications may be made. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims. Further, the above-described examples are for illustrative explanation of the present invention, and thus, the present invention is not limited thereto.

What is claimed is:

1. An air purifying apparatus for removing contaminants, the apparatus comprising:
    a housing, which is hollow, and comprises an inlet on one side and an outlet on another side;
    a ceramic filter including an elongated air flow path, and arranged in the housing, wherein the ceramic filter is configured to remove the contaminants by burning the contaminants included in contaminated air passing through the elongated air flow path; and
    a microwave generator configured to generate microwaves and to supply the generated microwaves to one end surface of the ceramic filter in a longitudinal direction thereof to heat the one end surface of the ceramic filter in the longitudinal direction.

2. The apparatus of claim 1, wherein a shielding member is mounted between the ceramic filter and the housing to prevent microwave and air leakage.

3. The apparatus of claim 1, wherein the housing comprises a shielding net at the inlet or the outlet to prevent microwave leakage.

4. The apparatus of claim 1, wherein the microwave generator is arranged outside the housing, wherein an inlet pipe is formed to be connected to the inside of the housing so that microwaves generated by the microwave generator flow into the housing.

5. The apparatus of claim 1, wherein the housing comprises a diffusion member configured to diffuse the microwaves generated by the microwave generator to transfer the microwaves to the one end surface of the ceramic filter.

6. The apparatus of claim 1, wherein the microwave generator supplies the microwaves to the other end surface of the ceramic filter in the longitudinal direction thereof to heat the other end surface of the ceramic filter in the longitudinal direction.

7. An air purifying apparatus, comprising:
    an air purifying device disposed between a first duct and a second duct that are arranged side by side, and configured to remove contaminants by burning contaminated air introduced through the first duct while the contaminated air is passed through the air purifying device, and to discharge the air to the second duct,
    wherein the air purifying device comprises:
    a housing, which is hollow, and has on one side an inlet through which the contaminated air is introduced, the inlet being connected to the first duct, and on the other side an outlet through which purified air is discharged, the outlet being connected to the second duct;
    a ceramic filter formed in a column shape, arranged in the housing, and having a plurality of elongated air passages, through which the contaminated air is passed, in a longitudinal direction; and
    a microwave generator configured to generate microwaves and to supply the generated microwaves to one end surface of the ceramic filter in the longitudinal direction thereof to heat the one end surface of the ceramic filter in the longitudinal direction.

* * * * *